United States Patent [19]

Kim et al.

[11] Patent Number: 5,698,592
[45] Date of Patent: Dec. 16, 1997

[54] MATERIALS AND METHODS FOR CONTROLLING NEMATODES

[75] Inventors: Leo Kim, Carlsbad; Jerald S. Feitelson, San Diego, both of Calif.; John Harvey, Bend, Oreg.; Paul S. Zorner, Carlsbad, Calif.

[73] Assignee: Mycogen Corporation, San Diego, Calif.

[21] Appl. No.: 731,719

[22] Filed: Oct. 17, 1996

Related U.S. Application Data

[63] Continuation-in-part of Ser. No. 546,053, Oct. 20, 1995.
[51] Int. Cl.⁶ .......................... A01N 37/00; A01N 37/02; A01N 37/06
[52] U.S. Cl. .................. 514/552; 514/30; 514/450; 514/529; 514/531; 514/546; 514/547; 514/548; 514/549; 514/557; 514/558; 514/560
[58] Field of Search .................. 514/546, 549, 514/552, 30, 450, 529, 531, 547, 548, 557, 558, 560

[56] References Cited

U.S. PATENT DOCUMENTS

| | | | |
|---|---|---|---|
| 2,852,426 | 9/1958 | Stansbury | 514/547 |
| 4,560,677 | 12/1985 | Dybas | 514/30 |

OTHER PUBLICATIONS

TarJan et al., Nematocidal Value of Some Fatty Acids, Bulletin 332, Contribution 884, Agricultural Experiment Station, University of Rhode Island, Kingston, 1956.

Stadler, M. et al., "Fatty acids and other Compounds with nematicidal activity From cultures of Basidiomycetes," Planta. Med., vol. 60, 1994, pp. 128–132.

Boyce Thompson Institute for Plant Research 58th Annual Report, 1981, pp. 13–16.

Malik, Z. et al., "Effect of pH and some mineral salts and fatty acids on survival of *Xiphinema americanrm*," Nematol. medit., vol. 12, 1984, pp. 73–79.

*Primary Examiner*—John Pak
*Attorney, Agent, or Firm*—Saliwanchik, Lloyd & Saliwanchik

[57] ABSTRACT

Methods and compositions for the control of nematodes are disclosed. Specifically, fatty acid ester compounds have been found to advantageously control nematodes at concentrations which are non-phytotoxic. The fatty acid ester compounds can be used in conjunction with other nematicidal agents such as free fatty acids, fatty acid salts, avermectins, ivermectin, and milbemycin.

17 Claims, No Drawings

MATERIALS AND METHODS FOR CONTROLLING NEMATODES

CROSS-REFERENCE TO A RELATED APPLICATION

This application is a continuation-in-part of co-pending application Ser. No. 08/546,053, fled Oct. 20, 1995.

BACKGROUND OF THE INVENTION

Nematodes are important plant pests which cause millions of dollars of damage each year to turf grasses, ornamental plants, and food crops. Efforts to eliminate or minimize damage caused by nematodes in agricultural settings have typically involved the use of soil fumigation with materials such as chloropicrin, methyl bromide, and dazomet, which volatilize to spread the active ingredient throughout the soil. Such fumigation materials can be highly toxic and may create an environmental hazard. Various non-fumigant chemicals have also been used, but these too create serious environmental problems and can be highly toxic to humans.

The accepted methodology for control of nematodes afflicting animals has centered around the use of the drug benzimidazole and its congeners. The use of these drugs on a wide scale has led to many instances of resistance among nematode populations (Prichard, R. K. et al. [1980] "The problem of anthelmintic resistance in nematodes," *Austr. Vet. J.* 56:239–251; Coles, G. C. [1986] "Anthelmintic resistance in sheep," In *Veterinary Clinics of North America: Food Animal Practice*, Vol 2:423–432 [Herd, R. P., Eds.] W. B. Saunders, New York).

A small number of research articles have been published concerning the effects of␦-endotoxins from *B. thuringiensis* species on the viability of nematode eggs. See, for example, Bottjer, Bone and Gill ([1985] *Experimental Parasitology* 60:239–244); Ignoffo and Dropkin (Ignoffo, C. M., Dropkin, V. H. [1977] *J. Kans. Entomol. Soc.* 50:394–398); and Ciordia, H. and W. E. Bizzell ([1961] *Jour. of Parasitology* 47:41 [abstract]). Several patents have issued describing the control of nematodes with B.t. See, for example, U.S. Pat. Nos. 4,948,734; 5,093,120; 5,281,530; 5,426,049; 5,439, 881; 5,236,843; 5,322,932; 5,151,363; 5,270,448; 5,350, 577.

The pesticidal activity of avermectins is well known. The avermectins are disaccharide derivatives of pentacyclic, 16-membered lactones. They can be divided into four major compounds: $A_{1a}$, $A_{2a}$, $B_{1a}$, and $B_{2a}$; and four minor compounds: $A_{1b}$, $A_{2b}$, $B_{1b}$, and $B_{2b}$.

The organism which produces avermectins was isolated and identified as *Streptomyces avermitilis* MA-4680 (NRRL;8165). Characteristics of the avermectin producing culture and the fermentation process are well documented and known to those skilled in the art. (Burg, R. W. et al. [1979] "Avermectins, New Family of Potent Anthelmintic Agents: Producing Organism and Fermentation," *Antimicrob. Agents Chemother.* 15(3):361–367). The isolation and purification of these compounds is also described in U.S. Pat. No. 4,310,519, issued Jan. 12, 1982.

Another family of pesticides produced by fermentation are the milbemycins, which are closely related to the avermectins. The milbemycins can be produced by a variety of Streptomyces and originally differed from the avermectins only in the C-13 position. The milbemycins and their many derivatives are also well known to those skilled in the art and are the subject of U.S. patents. See, for example, U.S. Pat. No. 4,547,520.

While the avermectins were initially investigated for their anthelmintic activities, they were later found to have other insecticidal properties, although the degree varies. The activity of avermectins must generally be determined empirically.

22,23-dihydroavermectin $B_1$ is a synthetic derivative of the avermectins and has been assigned the nonproprietary name of ivermectin. It is a mixture of 80% 22,23-dihydroavermectin $B_{1a}$ and 20% 22,23-dihydroavermectin $B_{1b}$. Ivermectin has been tested on a variety of laboratory and domestic animals for control of nematodes, ticks, and heartworms.

Avermectin $B_{2a}$ is active against the rootknot nematode, *Meloidogyne incognita*. It is reported to be 10–30 times as potent as commercial contact nematicides when incorporated into soil at 0.16–0.25 kg/ha (Boyce Thompson Institute for Plant Research 58th Annual Report [1981]; Putter, I. et al. [1981] "Avermectins: Novel Insecticides, Acaracides, and Nematicides from a Soil Microorganism," *Experientia* 37:963–964). Avermectin $B_{2a}$ is not toxic to tomatoes or cucumbers at rates of up to 10 kg/ha. Avermectin $B_1$ is a combination of avermectin $B_{1a}$ (major component) and avermectin $B_{1b}$. It has demonstrated a broad spectrum of insecticidal activities. The data indicate that avermectin $B_1$ is primarily a miticide, although it is also effective on the Colorado potato beetle, potato tuberworm, beet armyworm, diamondback moth, gypsy moth, and the European corn borer.

The use of avermectins in various agricultural applications has been described in publications and patents. The use of avermectin with spray oils (lightweight oil compositions) has been described. See, for example, U.S. Pat. No. 4,560, 677 issued Dec. 24, 1985; EPO applications 0 094 779 and 0 125 155; and Anderson, T. E., J. R. Babu, R. A. Dybas, H. Mehta (1986) *J. Econ. Entomol.* 79:197–201.

Fatty acids are a class of natural compounds which occur abundantly, in nature and which have interesting and valuable biological activities. The in vitro activity of fatty acids against many medically important fungi and bacteria is well known. There is a much smaller body of literature concerning the activity of fatty acids and their derivatives against pathogens on agricultural crops. Ahmed et al. (Ahmed, S. M., F. Abroad, S. M. Osman [1985] *JAOCS* 62:1578–1580) report in vitro inhibition of radial growth of several fungal genera with plant pathogenic representatives. Recently there has been an expanding use of "insecticidal soaps" in agriculture which are salts of certain fatty adds. Chase et al. (Chase, A. R., L. S. Osborne [1983] *Plant Disease* 67:1021–1023) observed that applications of an 18:1 fatty acid salt "insecticidal soap" gave moderate preventive control of two foliage plant diseases and actually exacerbated two other diseases. Nickel and silver salts of fatty acids have been used to control pathogens on plants: GB Patent Nos. 907,842 and 1,219,077. In U.S. Pat. No. 3,983,214, Misato et al. claim a fungicidal composition containing a sucrose fatty acid ester. In U.S. Pat. No. 4,771,571, Obrero et al. describe a method of preventing infections of pineapple by treating the fruit, while on the bush, with a surfactant. In U.S. Pat. No. 4,002,775, Kabara et al. claim microbicidal food additives comprising 1 or 2-mono-laurin polyol ester. The use of fatty acid esters and alcohols for the control of powdery mildew on apple buds has been described (Frick, E. L., R. T. Burchill [1972] *Plant Disease Reporter* 56:770–772; U.S. Pat. No. 3,931,413). In the '413 patent, Frick et al. emphasize the phytotoxicity of fatty acids and state that the acid or salt form should only be used on dormant plant tissue. The phytotoxicity of fatty acids and their salts is well documented and has long been believed to be a barrier to the use of these compositions on living p/ants. See U.S. Pat. No. 5,246,716. Tarjan and Cheo (Tarjan, A. C., P. C. Cheo [1956] "Nematocidal Value of Some Fatty Acids," Bulletin 332, Contribution 884, Agricultural Experiment Station, University of Rhode Island, Kingston, 41 pp.) report the activity of certain fatty acids against nematodes. Tarjan and Cheo do not disclose or suggest the use of fatty acid esters. In 1977 Sitaramaiah and Singh (Sitaramaiah, K, R. S. Singh [1977] *Indian J. Nematol.* 7:58–65) also examined the response of nematodes to fatty acids. These researchers examined the effects of low molecular weight acids such as acetic, formic, propionic, and butyric acids. The results of these tests with short chain acids were equivocal, showing nematode-inhibitory action in some instances and stimulatory activity in other instances. Phytotoxicity of these acids was observed at higher concentrations. These short chain fatty acids were also examined by Malik and Jairajpuri (Malik, Z., M. S. Jairajpuri [1977] *Nematol. medit.* 12:73–79), who observed nematode toxicity at high concentrations of the fatty acids. In 1987, Kiuchi et al. (Kiuchi, F., N. Miyashita, Y. Tsuda, K. Kondo, H. Yoshimura [1977] *Chem. Pharm. Bull.* 35:2880–2886) reported the anthelmintic effect of fatty acids obtained from betel nuts. The fatty acids were found to be toxic against larvae of worms which cause parasitic diseases in humans and animals. Stadler et al. (Stadler, M., A. Mayer, H. Anke, O. Sterner [1994] *Planta Med.* 60:128–132) studied fatty acids and other compounds with nematicidal activity which could be obtained from cultures of Basidiomycetes. Stadler et al. primarily evaluated long chain fatty acids having, for example, 16 to 18 carbons.

Fatty acid ester compositions have been described in U.S. Pat. No. 5,284,819, but this patent does not disclose or suggest the use of fatty acid esters to control nematodes.

BRIEF SUMMARY OF THE INVENTION

The subject invention concerns compositions and processes for controlling nematodes. In one embodiment, the subject invention comprises the use of certain fatty acid compounds to control nematodes which infest plants or the situs of plants. Nematodes afflicting animals can also be controlled using the methods and compositions of the subject invention. The fatty acid compounds useful according to the subject invention can be from about C8 to about C14 and can be, for example, in the epoxide, cyclopropane, methylated, or hydroxylated forms. In a preferred embodiment of the subject invention, fatty acid esters are used.

Preferred fatty acid compounds useful according to the subject invention can be represented by the following formula:

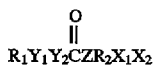

wherein $Z=O$, $NR_3$, or $S$ $Y_1=H$, C1–C5 hydrocarbon, or hydroxyl at any position along $R_1$ $Y_2=H$, C1–C5 hydrocarbon, or hydroxyl at any position along $R_1$ $X_1=H$, hydroxyl, or C1 to C3 hydrocarbon at any position along $R_2$ $X_2=H$, hydroxyl, or C1 to C3 hydrocarbon at any position along $R_2$.

$R_1$=C7 to C13 saturated or unsaturated hydrocarbon, or an epoxide, or cyclopropane thereof $R_2$=C1 to C10 saturated or unsaturated hydrocarbon $R_3$=$C_1$–$C_{10}$ saturated or unsaturated, branched or unbranched, hydrocarbon which may have one or more hydroxyl groups at any position on $R_3$; carbohydrate; a salt-forming moiety; or H.

As those skilled in the art would readily recognize, when Z=N, there will be two R groups attached to N. Thus, in this specific case of Formula I, the formula can be represented as follows:

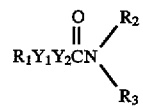

wherein $R_1$ C5 to C19 saturated or unsaturated hydrocarbon, or an epoxide, or cyclopropane thereof $Y_1=H$, $C_1$–$C_5$ hydrocarbon, or hydroxyl at any position along $R_1$ $Y_2=H$, $C_1$–$C_5$ hydrocarbon, or hydroxyl at any position along $R_1$ $R_2=C_1$–$C_{10}$ saturated or unsaturated, branched or unbranched, hydrocarbon which may have one or more hydroxyl groups at any position on $R_2$; carbohydrate; salt; or H;

$R_3=C_1$–$C_{10}$ saturated or unsaturated, branched or unbranched, hydrocarbon which may have one or more hydroxyl groups at any position on $R_3$; carbohydrate; salt; or H.

In a preferred embodiment of the subject invention, a C8 to C14 fatty acid ester is used. Advantageously, the ester may be a methyl ester or ethylene glycol ester.

The invention process is particularly valuable to control nematodes attacking the roots of desired crop plants, ornamental plants, and turf grasses. The desired crop plants can be, for example, tomatoes, potatoes, or strawberries.

In one embodiment of the subject invention, the fatty acid compound is used in conjunction with another nematicidal agent. The other nematicidal agent may be, for example, a biological agent, an avermectin, or a milbemycin.

DETAILED DISCLOSURE OF THE INVENTION

The process of the subject invention concerns the use of fatty acid compounds to control the infestation of plants or animals by nematodes. In a preferred embodiment of the subject invention, the fatty acid compound is a C8 to C14 fatty acid ester. C9 to C12 fatty acid esters are particularly preferred. The fatty acid esters used according to the subject invention can be unsubstituted, or substituted, saturated, or unsaturated. The fatty acid component used according to the subject invention may be a single fatty acid ester or a mixture of two or more fatty acid esters. The fatty acid ester may be used in conjunction with other fatty acid compounds, including the free acids and salts. The salts may be, for example, sodium or potassium salts, or ammonium salts.

Fatty acid compounds specifically exemplified herein include the methyl ester of pelargonic acid (PAME), ethylene glycol ester of pelargonic acid (PAEGE), and methyl ester of lauric acid (C12) (LAME).

The fatty acid compounds used in the invention can be applied to animals, plants, or to the situs of plants needing nematode control. The fatty acid compositions may be applied by, for example, drip and drench techniques. With the drip application, the fatty acid composition can be applied directly to the base of plants or to the soft immediately adjacent to the plants. The composition may be applied through already existing drip irrigation systems. This procedure is particularly applicable for ornamental plants, strawberries, tomatoes, potatoes, and vegetables. Alternatively, a drench application can be used. For plants, a sufficient quantity of the fatty acid composition is applied such that the composition drains to the root area of the plants. An important aspect of the subject invention is the surprising discovery that certain fatty acid compounds have excellent nematicidal activity at concentrations which are not phytotoxic. The drench technique can be used for a variety of crops and for turf grasses. The drench technique can also be used for animals. Preferably, the fatty acid composition would be administered orally to facilitate activity against internal nematode parasites. The compositions of the subject invention can readily be applied using the teachings provided herein.

In a preferred embodiment of the subject invention, a fatty acid ester compound will be applied as an aqueous microemulsion. As described herein, the concentration of the fatty acid ester should be sufficient to control the nematode infestation without causing phytotoxicity to the desired plants. The concentration of fatty acid ester may be, for example, from about 0.001% to about 2%, preferably from about 0.025% to about 1%, and, most preferably, from about 0.05% to about 0.5%. The concentration of the fatty acid ester can be reduced by using the ester in conjunction with another fatty acid compound such as the free fatty acid or a salt.

The fatty acid composition used according to the subject invention can be applied in conjunction with another nematicidal agent. The second nematicidal agent may, for example, be applied simultaneously or sequentially with the fatty acid ester. Such other nematicidal agents include, for example, avermectins. The avermectin compound used according to the subject invention may be any of the avermectins, milbemycins, or derivatives of either, having activity against nematodes. The avermectin's activity will be enhanced when combined with a fatty acid compound as described herein. Thus, the specific combination of ingredients can be manipulated to provide the optimal composition for a particular application.

Standard concentrations of avermectins are well known to those skilled in the art. For example, the avermectin compounds can be employed in the combination of the subject invention at concentrations of from about 0.03 to about 110 parts per million (ppm). Preferably, from about 1 to about 5 ppm are employed.

As would be readily appreciated by a person skilled in the art, the delivery of the fatty acid and/or avermectin compound can be calculated in terms of the active ingredient applied per unit area. For example, the fatty acid may be applied at a rate of about 0.02 lb/acre to about 0.1 lb/acre and, preferably, from about 0.5 lb/acre to about 2 lbs/acre. Similarly, the avermectin product can be applied at a rate of up to about 16 oz. of formulated product ("AVID," available from Merck) per acre. Preferably, about 4 oz. to about 8 oz. formulated "AVID" per acre would be used. Thus, the avermectin compound can be applied up to about 0.02 lb/acre. Preferably, the rate of avermectin is between about 0.005 lb/acre and 0.01 lb/acre. A person of ordinary skill in the art would readily appreciate that the desired application rate of the active ingredients could be achieved using a great variety of different concentrations of active ingredients while varying the application rate of the solution. Thus, a large quantity of dilute solution could be applied or a smaller quantity of a more concentrated solution.

A variety of different avermectins or related compounds can be used according to the subject invention. Ivermectin may also be used according to the subject invention, as may the milbemycins. For brevity, the term "avermectin" is used herein to refer to all the avermectins and their derivatives as well as related compounds such as the milbemycins and the ivermectins. "Derivatives" refer to chemical modifications of the avermectins or milbemycins which are well known and available to those skilled in this art. Such derivatives are described, for example, in U.S. Pat. No. 4,560,677. Avermectin is readily available under a variety of tradenames including "AVID," "ZEPHYR," "VERTIMEC," and "AGRI-MEK."

The fatty acid compositions of the subject invention may also be used in conjunction with nematicidal agents other than the avermectins. For example, the fatty acid compounds may be used with biological agents such as *Bacillus thuringiensis* or with nematicidal fungi. In this context, the fatty acid composition could be applied at concentrations which would not antagonize the action of the biological agent. The biologically active agent may be in a live proliferative form or may be in a dead stabilized form as described, for example, in U.S. Pat. Nos. 4,695,462 and 4,695,455. Furthermore, the fatty acid compositions of the subject invention may be used with plants which are specifically bred or engineered for nematode resistance. The plants may, for example, be transformed with B.t. genes which confer nematode resistance or may simply be hybrids or varieties selected for such resistance. The fatty acid compositions of the subject invention are particularly effective against free-living ectoparasitic nematodes and, therefore, combined use with plants selected for endoparasitic nematode resistance is highly advantageous.

Following are examples which illustrate procedures for practicing the invention. These examples should not be construed as limiting. All percentages are by weight and all solvent mixture proportions are by volume unless otherwise noted.

EXAMPLE 1

Preparation of Fatty Acid Esters

Synthesis of ethylene glycol monopelargonate. 51.5 g pelargonic acid, and 51 g ethylene glycol were dissolved in 200 ml of dichloromethane, and 20 drops of $H_2SO_4$ were added to the mixture. It was stored at room temperature for 6 days. After 6 days, 150 ml of 0.1 N NaOH was added to the reaction mixture, which was then vigorously shaken. The dichloromethane layer (lower layer) was collected and washed with saturated NaCl solution.

After drying on $Na_2SO_4$, the chloroform layer was evaporated. Remaining oil (38 g) was subjected to vacuum distillation, yielding 34.8 g (yield 53.8%) of ethylene glycol monopelargonate (b.p. 135°–137° C. [7 mm Hg]).

Synthesis of methyl ester of pelargonic acid. The methyl ester of pelargonic acid can readily be produced using procedures well known to those skilled in the art. One such procedure would be analogous to that used to produce the ethylene glycol monopelargonate. For example, about 51 g of pelargonic acid and 51 g of methyl alcohol can be dissolved in about 200 ml of dichioromethane to which 20 drops of $H_2SO_4$ are added. The mixture can be stored at room temperature for 6 days, at which time 150 ml of NaOH is added to the reaction mixture, which is then vigorously shaken. The dichloromethane layer (lower layer) is collected and washed with saturated NaCl solution.

After drying on $Na_2SO_4$, the chloroform layer is evaporated. Remaining oil is then subjected to vacuum distillation, yielding the methyl ester of pelargonic acid.

Synthesis of the esters of $C_6$ to $C_{14}$ acids.

(a) Hexanoic acid ($C_6$ acid) and heptanoic acid ($C_7$ acid)—each of 100 mmol of $C_6$ and $C_7$ acids were added to 300 mmol of ethylene glycol. Several drops of $H_2SO_4$ were added to the mixture and stored at room temperature for 9 days. Isolation of the esters can be carried out using the same procedure as that to isolate ethylene glycol monopelargonate.

(b) Decanoic acid ($C_{10}$ acid), dodecanoic acid ($C_{12}$ acid), and tetradecanoic acid ($C_{14}$ acid)—each of 100 mmol of $C_{10}$, $C_{12}$ and $C_{14}$ acids were dissolved in 50 ml dichloromethane, and 300 mmol of ethylene glycol were added to the solutions. Several drops of $H_2SO_4$ were added to the mixture. The reaction mixtures were stored at room temperature for 9 days. Isolation of the esters were carried out using the same procedure as that to isolate ethylene glycol monopelargonate.

A variety of fatty acid esters useful according to the subject invention can be readily prepared by a person skilled in this art having the benefit of the subject disclosure.

EXAMPLE 2

Nematicidal Activity of Fatty Acid Compositions

Caenorhabditis elegans was grown for 5 days at 18° C., 150 rpm, feeding on E. coli strain MC1061 in submerged batch culture in 2 L flasks according to The Nematode Caenorhabditis elegans (1988) Cold Spring Harbor Laboratory Press, p. 602.

Ten milliliters of culture were removed, briefly centrifuged (1,500 rpm, 2 minutes, room temperature) and the nematodes resuspended in 10 ml of M9 broth. One and a half milliliters of nematodes were added to 9.3 ml of stationary phase MC1061 E. coli cells in L-broth, and divided into 150 µl aliquots in 24-well tissue culture plates. Each well contained approximately 25 mixed stage (L1-adult hermaphrodite) nematodes.

To each well, 150 µl of fatty acid dilutions or controls were added and quickly mixed by gentle swirling. Nematode viability was scored by visual examination under a 100x dissecting microscope, and prodding with 31-gauge platinum wire. A 5-point viability scoring system was used as follows:

1: no effect
2: <10% dead, some ring-shaped worms, mostly highly active
3: some motile worms, most stiff and immobile
4: >90% stiff and immobile (a few twitching larvae)
5: 100% stiff and immobile, no signs of life.

Intermediate scores, e.g., 3.5, were given when appropriate.

Four fatty acid compounds were tested at five rates in triplicate, with a formulation blank. Viability was scored at 3 minutes, 30 minutes, and 1 hour after compound addition. Viability scores of triplicate samples were averaged.

The compounds tested were methyl ester of pelargonic acid (C9) (PAME), ethylene glycol ester of pelargonic acid (C9) (PAEGE), pelargonic acid (C9) (PA), and methyl ester of lauric acid (C12) (LAME). The results of this test are shown in Table 1.

The most toxic fatty acid to the nematode species tested was PAME (methyl ester of pelargonic acid; C9), with nearly complete kill at 0.005% at 3 minutes and complete kill at this concentration after 30 minutes. At the 30 minute time point, the second most nematicidal compound tested was LAME (methyl ester of lauric acid; C12). This compound killed more completely, but slightly more slowly than PAEGE (ethylene glycol ester of pelargonic acid; C9).

TABLE 1

Caenorhabditis elegans results

| Compound | Concentration | 3 min | 30 min | 1 hour |
|---|---|---|---|---|
| PAME (C9-methyl ester) | 0.1% | 4.0 | 5.0 | 5.0 |
| | 0.05% | 4.0 | 5.0 | 5.0 |
| | 0.025% | 4.0 | 5.0 | 5.0 |
| | 0.005% | 4.0 | 5.0 | 5.0 |
| | 0.0025% | 3.7 | 4.8 | 4.8 |
| PAEGE (C9-ethylene glycol ester) | 0.1% | 3.8 | 5.0 | 5.0 |
| | 0.05% | 3.2 | 4.7 | 4.7 |
| | 0.025% | 3.0 | 4.5 | 4.5 |
| | 0.005% | 1.2 | 2.5 | 2.7 |
| | 0.0025% | 1.0 | 2.0 | 2.2 |
| PA (C9-free acid) | 0.1% | 4.0 | 5.0 | 5.0 |
| | 0.05% | 1.5 | 4.7 | 4.7 |
| | 0.025% | 1.2 | 2.3 | 2.8 |
| | 0.005% | 1.5 | 1.5 | 3.5 |
| | 0.0025% | 1.5 | 1.5 | 3.7 |
| LAME (C12-methyl ester) | 0.1% | 2.2 | 5.0 | 5.0 |
| | 0.05% | 2.5 | 4.5 | 4.8 |
| | 0.025% | 2.5 | 4.8 | 5.0 |
| | 0.005% | 2.0 | 4.7 | 4.7 |
| | 0.0025% | 1.3 | 2.8 | 3.8 |
| Formulation | blank | 1.0 | 2.5 | 3.2 |
| Water | blank | 1.0 | 1.5 | 1.8 |

EXAMPLE 3

Activity Against the Common Lance Nematode (Hoplolaimus galeatus) In Vitro

Nematodes were observed for obvious behavioral changes and mortality in a serial dilution series of PAME in a water suspension, in which the final concentration of PAME ranged from 0.4 ppm to 0.5%. Rate/time relationships were determined to derive inhibition of activity and mortality; reversibility of effects was also examined. Six treatments of four repetitions were performed, with each trial repeated once. Trials 1a and 1b had exposure times of 1–2 hours and 24 hours, respectively. Trial 2 had data taken approximately 48 hours after treatment.

TABLE 2

| Trial 1a - 1–2-hour exposure: Hoplolaimus galeatus | | | |
|---|---|---|---|
| PAME Dose (ppm) | Total # dead | Total # tested | % dead |
| 5,000 | 67 | 67 | 100.0 |
| 1,000 | 124 | 127 | 97.7 |
| 100 | 165 | 175 | 94.3 |
| 4 | 24 | 219 | 11.0 |
| 0.4 | 8 | 163 | 4.9 |
| 1/0 dil. blank | 6 | 163 | 3.7 |
| water | 7 | 179 | 3.9 |

At 5,000 ppm, nematodes were stiff/arcuate within 5 minutes of treatment, evidence of mortal effect. At 1,000 ppm, nematodes were not coiling after 30 minutes, but were more agitated in body movement than untreated nematodes. By 40 minutes after treatment with 100 ppm, nematodes were unnaturally stiff with an arcuate body posture or moving very slowly; within another 10 minutes, half did not respond to needle prodding. In those PAME treatments that affected nematodes quickly, males and juveniles seemed to die more quickly than adult females. By 3.5–4.0 hours after treatment with 4 ppm, nematodes moved reluctantly and weakly, though most were still alive.

TABLE 3

Trial 1b - 24-hour exposure: *Hoplolaimus galeatus*

| PAME Dose (ppm) | Total # dead | Total # tested | % dead |
|---|---|---|---|
| 5,000 | 74 | 74 | 100.0 |
| 1,000 | 161 | 161 | 100.0 |
| 100 | 181 | 184 | 98.4 |
| 4 | 24 | 215 | 11.2 |
| 0.4 | 9 | 161 | 5.6 |
| 1/0 dil blank | 13 | 166 | 7.8 |
| water | 10 | 181 | 5.5 |

After 24 hours, nematodes at 0.4 ppm and untreated control were alive and looked normal. Many of the nematodes treated at 4 ppm were crystalline and stiff, although most responded very slowly to physical prodding. Most of the nematodes at 100 ppm were unresponsive to prodding, had an arcuate posture, looked clear, crystalline, and often vacuolate. The most lethal effects were already expressed within 4 hours of treatment. There was no indication of reversal of any effect. The $LC_{50}$ was between 4 and 100 ppm.

TABLE 4

Trial 2 - 48-hour exposure: *Hoplolaimus galeatus*

| PAME Dose (ppm) | Total # dead | Total # tested | % dead |
|---|---|---|---|
| 64 | 134 | 175 | 76.6 |
| 32 | 21 | 104 | 20.2 |
| 16 | 28 | 188 | 14.9 |
| 8 | 27 | 192 | 14.1 |
| 4 | 18 | 190 | 9.5 |
| 2 | 8 | 185 | 4.3 |
| 1/0 dil blank | 29 | 191 | 15.2 |
| water | 13 | 177 | 7.3 |

Trends were similar to those observed for Trial 1. There was essentially no effect from doses of 2 and 4 ppm, a mild effect comparable to the formulation blank at doses of 8 and 16 ppm, and the principal lethal effect took place above 32 ppm.

EXAMPLE 4

Activity Against the Common Lance Nematode (*Hoplolaimus galeatus*) and Stunt Nematode (*Tylenchorhynchus dubius*) on Turf in Pots PAME was tested at several concentrations (10,000, 1,000, 10, and 1 ppm) on turf grass grown in pots, along with a formulation blank and water controls, for activity against *Hoplolaimus galeatus* and *Tylenchorhynchus dubius* at one, two, and three weeks. Additionally, the fatty acid compound at the highest concentration, the full-strength blank, and a 1/10 diluted blank were tested as a multiple treatment. Appropriate dilutions of the fatty acid compound were made in water and applied as a drench in 50-ml aliquots to six replicates of each nematode strain in 130 cc of soil per pot for each time frame. Treatment was retained in each pot for 15 minutes by the presence of a "PARAFILM" wrap. After the "PARAFILM" was removed, the pots were allowed to drain and the soil was seeded with *Poa annua* based on a rate of 3 lbs of seed per 1000 square feet. The controls were applied and seeded in an identical manner. Pots were transferred to a greenhouse where single treatment pots were irrigated with 50 ml per pot three time a week until termination of the experiment. Multiple drench pots were treated three times per week with the appropriate treatment. A "PARAFILM" wrap was applied and left in place for 15 minutes at each retreatment. Enumeration of nematode populations at one, two, and three weeks was by sucrose density gradient centrifugation followed by counting on a grid plate.

At 7 DAT, no germination of grass seed was observed with 10,000 ppm (1%) PAME nor with the full-strength blank, with single and multiple drenches each. All other treatments had germinating grass seed. At 10 DAT, the single blank treatment grass germinated but appeared unhealthy. At 17 DAT, grass germinated in single drench 1% PAME but not in multiple drench 1% PAME. Thus, full-strength blank and 1% PAME strongly inhibited seed germination, though 1% PAME was not phytotoxic to rye grass seedlings in another test.

Both ectoparasitic species were clearly susceptible to PAME in these pot tests. At 3 weeks after infestation, single PAME applications at concentrations of 100–1000 ppm were statistically separable from the water controls.

EXAMPLE 5

Activity Against the Root-Knot Nematode (*Meloidogyne javanica*) Semi-In Vitro Test on Tomato Freshly hatched juveniles (J2) were incubated in dilutions of PAME at room temperatures for 4 hours and then 500 treated J2 in test solution were added to sand in a 4-dram glass vial that contained a tomato seedling. The number of galls induced by *M. javanica* per tomato root system was assayed at 10 days after incubation (means of three tests).

TABLE 5

| *Meloidogyne javanica* on tomato seedlings | | | |
|---|---|---|---|
| PAME dose (ppm) | Nema* | Phyto+ | mean # galls |
| 10,000 | D | TP | — |
| 5,000 | D | TP | — |
| 2,500 | D | TP | — |
| 1,250 | D | MP | 0 |
| 625 | D | MP | 0.3 |
| 320 | D | LP | 0 |
| 160 | D | N | 1.0 |
| 80 | D | N | 0.3 |
| 40 | D | N | 6.3 |
| 20 | D | N | 10.0 |
| 1/8 dil. blank | LV | LP | 12.3 |
| 1/16 dil. blank | LV | N | 12.0 |
| water | L | N | 14.7 |

*Nema: J2 were observed for viability under the dissecting microscope after 4 hours incubation in test compound.
D = nematodes appeared dead.
V = nematodes vacuolated; poor health, but viable.
L = nematodes living (healthy).
+Phyto: Phytotoxicity for each tomato seedling was monitored after application of nematodes in test solution.
TP = total phytotoxicity; plant shriveled up and died within several days.
MP = moderate phytotoxicity; plant quickly yellowed and became necrotic by end of test.
LP = light phytotoxicity; some leaf yellowing, but plant relatively healthy.
N = no apparent phytotoxicity.

PAME was particularly impressive in both its visual effects on root-knot nematode J2 and its reduction in nematode infection of tomato roots (galls). Worms at the higher PAME concentrations were sigmoid, nonmotile, and could not be revived in water; usually dead nematodes are straight. The 1/16 diluted formulation blank had little effect on worms or plants.

EXAMPLE 6

Activity Against the Soybean Cyst Nematode
(*Heterodera glycines*): Pot Tests in the Greenhouse Single plants of Lee68 soybean were germinated and grown in 15 cm diameter clay pots for two weeks prior to infestation of soil at the base of each plant with approximately 10,000 eggs of soybean cyst nematode Race 1. For each concentration of PAME, three soil types (sand/soil; 25/75, 50/50, 75/25) were tested and four replicates of each treatment were included. PAME was added at the specified concentrations (1250, 625, 320, 160, and 80 ppm) as a soil drench when SCN eggs were added to soil, and chemical applications were made similarly at weekly intervals for the next seven weeks. A "water" treatment and the formulation blank diluted with water were included as controls. At eight weeks after SCN inoculation, plants were harvested, cysts extracted from soil and roots, and data compiled.

TABLE 8

Greenhouse pot test: *Heterodera glycines* (SCN) on soybean seedlings

| PAME conc. (7 doses) | % sand/ % soil | Phyto* | mean total # cysts per root system | mean # cysts per gram root | % total cyst reduction (from water) |
|---|---|---|---|---|---|
| 1,250 ppm | 25/75 | high | 27 | 3 | 98.1 |
| (2 doses only) | 50/50 | high | 26 | 1 | 98.3 |
|  | 75/25 | high | 1 | 1 | 99.9 |
| 625 ppm | 25/75 | high | 24 | 9 | 98.3 |
|  | 50/50 | high | 5 | 1 | 99.7 |
|  | 75/25 | high | 5 | 1 | 99.7 |
| 320 ppm | 25/75 | low | 43 | 1 | 97.0 |
|  | 50/50 | low | 260 | 4 | 83.1 |
|  | 75/25 | low | 242 | 3 | 87.6 |
| 160 ppm | 25/75 | none | 589 | 7 | 58.2 |
|  | 50/50 | none | 1646 | 21 | (6.8) |
|  | 75/25 | none | 702 | 9 | 64.1 |
| 80 ppm | 25/75 | none | 856 | 15 | 39.3 |
|  | 50/50 | none | 2174 | 22 | (41.1) |
|  | 75/25 | none | 2284 | 21 | (16.6) |
| 1/16 dil. blank | 25/75 | none | 1099 | 17 | 22.1 |
|  | 50/50 | none | 2314 | 21 | (50.2) |
|  | 75/25 | none | 2388 | 23 | (22.0) |
| water | 25/75 | none | 1410 | 16 | — |
|  | 50/50 | none | 1541 | 28 | — |
|  | 75/25 | none | 1958 | 32 | — |

*Phyto:
high = plants almost completely dead.
moderate = plant stunted and necrotic.
low = plants usual size with some slight chlorosis of lower leaves.
none = no apparent phytotoxicity.

The lowest phytotoxicity and the lower numbers of cysts occurred in the 25/75 (sand/soil) mix within the same chemical treatment class. The 320 ppm treatment had only low phytotoxicity; the plants were not stunted but some leaf chlorosis was noted. Root and shoot weights for the 320 ppm plants were generally less than the lower PAME concentrations and controls, even though the plants were visually very similar. The formulation blank at 16-fold dilution had no deleterious effects on plant or nematode growth.

The 320 ppm rate gave the best control of SCN with little plant damage, both on a total cyst count and by the number of cysts per gram of root. The 160 ppm treatment also gave moderate control of SCN, and no plant damage was observed.

EXAMPLE 7

Additional Phytotoxicity Evaluations

First, 25 ml of 0.2% fatty acid solutions, or 1/10 diluted surfactant control, were carefully added by pipette to the soil of tomato plantlet soil "six-packs," each about 4-5" high. This quantity of liquid was sufficient to cause a slight amount of runoff. Care was taken to avoid application to stems or leaves, in order to determine the effects on plantlet roots.

Second, 5 ml of 0.2% fatty acid solutions, or 1/10 diluted surfactant control, were pipetted on the leaves, though much of the material ran off. All tomato plants were placed in regulated growth chambers, at 75° C., on a 16-hour light/8 hour dark cycle.

Tomato plants treated with fatty acids or surfactant controls were scored 40 hours after application. The only effects seen were with the highest rates of pelargonic acid (PA). At a 0.2% rate in soil, plant stems lost turgor and the plantlets drooped, though no browning was seen. The same concentration applied directly to leaves causes obvious wilting, though again no necrotic lesions were observed.

None of the other fatty acid treatments, even at the highest rates tested (0.2%) had any apparent effects on tomato plants. With PAME and LAME, at least 40-fold higher concentrations are required for phytotoxicity than for complete nematode kill in 30 minutes. Thus, the fatty acid ester compositions of the subject invention have an excellent "therapeutic ratio" for control of nematodes.

EXAMPLE 8

Fatty Acid Microemulsions

The following microemulsions can be utilized according to the subject invention for the control of nematodes:

| 1. Methyl pelargonate (PAME) | |
|---|---|
| Methyl nonanoate | 1.00% |
| Igepal CO 630 | 2.00% |
| Water | 85.00% |
| Isopropyl alcohol | 12.00% |
| 2. Ethylene glycol pelargonate (mono ester) (PAGE) | |
| Ethylene glycol pelargonate | 1.00% |
| Igepal CO 630 | 2.00% |
| Water | 85.00% |
| Isopropyl alcohol | 12.00% |
| 3. Methyl laurate (LAME) | |
| Methyl laurate | 1.00% |
| Igepal CO 630 | 2.00% |
| Water | 92.00% |
| Isopropyl alcohol | 5.00% |
| 4. Pelargonic acid (PA) | |
| Pelargonic acid | 1.00% |
| Igepal CO 630 | 7.80% |
| Water | 79.00% |
| Isopropyl alcohol | 12.00% |
| 5. Methyl soyate | |
| Methyl soyate | 1.00% |
| Igepal CO 630 | 5.00% |
| Water | 95.00% |

The active ingredients can be mixed with a surfactant such as Igepal CO 630 or any other member of the same family of surfactants having greater of lesser degrees of ethyoxylation. These surfactants are well known to those skilled in the art. Water is then added with vigorous stirring, and then isopropyl alcohol or other appropriate co-solvent is added. In the case of methyl soyate, no co-solvent was required to develop the microemulsion.

The major reason for using relatively low concentration microemulsions as the "starting" concentrate is to ensure that, upon dilution, a microemulsion is still retained. Higher concentration concentrates when diluted will generally result in colloidal emulsions that defeat the purpose. This composition ensures that a microemulsion reaches the nematode rather than a much larger, less "solubilized" fatty acid ester active ingredient. The microemulsified fatty acid dimensions are much closer to molecular dimensions and, as such, functions much like a "water soluble" component.

All five of these microemulsion preparations were highly stable, and maintained a completely transparent and clear appearance at room temperature. Earlier work, as exemplified by Tarjan & Cheo, supra, showed decreasing nematicidal activity as the emulsion appearance changed with increasing emulsifier concentration from white opaque to semi-transparent to transparent to completely clear. Thus, the biological activity obtained with the microemulsion technology of the subject invention was an unexpected result that is against the previous teachings.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for controlling nematodes, wherein said method comprises applying to said nematodes or to the situs of said nematodes, an effective amount of a microemulsion comprising about 2% v/v or less of a C8 to C14 fatty acid ester, wherein said fatty acid ester has the following formula:

$$R_1Y_1Y_2\overset{O}{\overset{\|}{C}}ZR_2X_1X_2$$

wherein

Z=O $Y_1$=H, C1–C5 hydrocarbon, or hydroxyl at any position along $R_1$ $Y_2$=H, C1–C5 hydrocarbon, or hydroxyl at any position along $R_1$ $X_1$=H, hydroxyl, or C1 to C3 hydrocarbon at any position along $R_2$ $X_2$=H, hydroxyl, or C1 to C3 hydrocarbon at any position along $R_2$ $R_1$=C7 to C13 saturated or unsaturated hydrocarbon, or an epoxide, or cyclopropane thereof $R_2$=C1 to C10 saturated or unsaturated hydrocarbon.

2. The method, according to claim 1, wherein $R_1$ is C8 to C11;

$Y_1=Y_2$=H;

$X_1$=H or hydroxyl; and $X_2$=H or hydroxyl.

3. The method, according, to 2, wherein said ester is selected from the group consisting of the methyl esters of C9 to C12 fatty acids, and the ethylene glycol esters of C9 to C12 fatty acids.

4. The method, according to claim 1, wherein said fatty acid ester is applied as an aqueous microemulsion with a co-solvent and a surfactant.

5. The method, according to claim 1, wherein said fatty acid ester is applied at a concentration of about 0.001% to about 2%.

6. The method, according to claim 5, wherein said fatty acid ester is applied at a concentration of about 0.05% to about 0.5%.

7. The method, according to claim 1, wherein said method further comprises applying a second nematicidal agent, which is utilized in conjunction with said fatty acid ester.

8. The method, according to claim 7, wherein said second nematicidal agent is selected from the group consisting of avermectins, ivermectin, and milbemycins.

9. The method, according to claim 8, wherein said avermectin, ivermectin, or milbemycin is present at a concentration between about 3 ppm and about 110 ppm.

10. The method, according to claim 8, wherein said avermectin, ivermectin, or milbemycin is applied at a rate of about 0.0006 lbs/acre to about 0.02 lbs/acre.

11. The method, according to claim 1, wherein said fatty acid ester is applied at a rate of at least about 0.02 lb/acre.

12. The method, according to claim 1, wherein said method further comprises applying a free fatty acid or fatty acid salt.

13. The method, according to claim 1, wherein said nematodes infest plants.

14. The method, according to claim 13, wherein said plant is soybean and said nematode is *Heterodera glycines.*

15. The method, according to claim 13, wherein said plant is tomato and said nematode is *Meloidogyne javonica.*

16. The method, according to claim 13 wherein said plant is turf grass and said nematode is *Hoplolaimus galeatus.*

17. The method, according to claim 13, wherein said plant is turf grass and said nematode is *Tylenchorhynchus dubius.*

* * * * *

UNITED STATES PATENT AND TRADEMARK OFFICE
CERTIFICATE OF CORRECTION

PATENT NO. : 5,698,592

DATED : December 16, 1997

INVENTOR(S) : Kim *et al.*

It is certified that error appears in the above-identified patent and that said Letters Patent is hereby corrected as shown below:

Column 1, line 8: "fled" should read --filed--;

line 33: "8-endotoxins" should read --δ-endotoxins--; and line 51: "(NRRL; 8165)" should read --(NRRL-8165)--.

Column 2, line 43: "Abroad" should read --Ahmad--.

Column 3, line 2: "p/ants" should read --plants--.

Column 4, line 19: "$R_1C5$" should read --$R_1 = C5$--.

Column 5, line 2: "soft" should read --soil--.

Column 6, line 64: "dichioromethane" should read --dichloromethane--.

Column 10, line 1: "Pots Were" should read --Pots were--.

Signed and Sealed this

Tenth Day of March, 1998

*Attest:*

BRUCE LEHMAN

*Attesting Officer*     *Commissioner of Patents and Trademarks*